US006797680B2

United States Patent
Chapaton et al.

(12) United States Patent
(10) Patent No.: US 6,797,680 B2
(45) Date of Patent: Sep. 28, 2004

(54) TRACTION FLUID WITH DI-ACID ESTER BRIDGED DIMER

(75) Inventors: Thomas J. Chapaton, Sterling Heights, MI (US); Tenneille Weston Capehart, Rochester, MI (US); James L. Linden, Rochester Hills, MI (US); Andrew Mark Mance, Royal Oak, MI (US)

(73) Assignee: General Motors Corporation, Detroit, MI (US)

( * ) Notice: Subject to any disclaimer, the term of this patent is extended or adjusted under 35 U.S.C. 154(b) by 0 days.

(21) Appl. No.: 10/359,027

(22) Filed: Feb. 5, 2003

(65) Prior Publication Data

US 2004/0152607 A1 Aug. 5, 2004

(51) Int. Cl.[7] ............................................. C10M 105/36
(52) U.S. Cl. ......................................... 508/496; 252/79
(58) Field of Search ........................................ 508/496

(56) References Cited

U.S. PATENT DOCUMENTS

| 4,371,726 A | | 2/1983 | Horita et al. ................... 585/3 |
|---|---|---|---|
| 4,786,427 A | * | 11/1988 | Dare-Edwards ............. 508/469 |
| 4,886,613 A | * | 12/1989 | Yoshimura et al. ........... 252/79 |
| 4,886,614 A | * | 12/1989 | Yoshimura et al. ........... 252/79 |
| 4,889,650 A | * | 12/1989 | Yoshimura et al. ........... 252/79 |
| 5,039,440 A | * | 8/1991 | Yoshimura et al. ........... 252/79 |
| 5,075,024 A | * | 12/1991 | Yoshimura et al. ........... 252/79 |
| 5,085,792 A | * | 2/1992 | Narihiko et al. ............... 252/79 |
| 5,171,481 A | * | 12/1992 | Yoshimura et al. ......... 508/463 |
| 5,259,978 A | * | 11/1993 | Yoshimura et al. ........... 252/79 |
| 5,318,711 A | * | 6/1994 | Evans et al. ................. 508/485 |
| 6,187,979 B1 | | 2/2001 | Ido et al. ....................... 585/10 |
| 6,395,689 B1 | | 5/2002 | Wagner et al. .............. 508/580 |
| 6,638,417 B2 | * | 10/2003 | Ishida et al. .................. 208/19 |

FOREIGN PATENT DOCUMENTS

| EP | 0266848 | 11/1987 |
|---|---|---|
| EP | 0402881 | 6/1990 |
| EP | 0508292 | 4/1992 |
| EP | 0526218 | 7/1992 |

OTHER PUBLICATIONS

"A Novel Family of Traction Fluids Deriving from Molecular Design", M. P. Dare–Edwards, Shell Chemicals, London, UK, pp. 197–205.

* cited by examiner

*Primary Examiner*—Ellen M McAvoy
(74) *Attorney, Agent, or Firm*—Kathryn A. Marra

(57) ABSTRACT

The present invention includes a traction fluid that includes a di-acid ester bridged dimer. Methods of using di-acid ester bridged dimers in traction fluids are also disclosed.

10 Claims, 3 Drawing Sheets

TRACTION FLUID WITH DI-ACID ESTER BRIDGED DIMER

FIELD OF THE INVENTION

This invention relates to compounds, compositions and methods of using the compounds and compositions as traction fluids in toroidal continuously variable transmission (T-CVT) systems.

BACKGROUND OF THE INVENTION

A T-CVT system includes an input disk connected to the engine, an output disk connected to the wheels, and a pair of power rollers which engage the two disks and transfer drive power from the input disk to the output disk. A lubricant, called a traction fluid, lubricates the system and prevents the rollers from contacting the disks. Because the disks and roller never physically touch, the traction fluid also transfers drive power from the input disk to the rollers and then to the output disk. This contradiction of purposes leads to the adversarial nature of the physical properties needed by a traction fluid.

One constraint is the ability of any particular traction fluid to transfer power among the components of the T-CVT system. This ability is represented by the traction coefficient ($\mu_T$). The drive power is directly proportional to the $\mu_T$, thus a higher $\mu_T$ is advantageous.

Another constraint on the physical properties of a traction fluid is the range of. temperatures at which a T-CVT must be operational. Start-up operating temperatures of T-CVT's may be as low as −40° C., while operating temperature could be as high as 140° C. Normal operating conditions will be in the range of 90° to 110° C. At the low end of the temperature range, the traction fluid must have a viscosity which is low enough to allow the traction fluid to flow and be pumped. At the high end of the range, the viscosity must be high enough to provide adequate lubrication. A flash point above 150° C. is desirable. In between the extremes of temperature, it is desirable to have the IT of the traction fluid independent of temperature. Furthermore, the viscosity of the traction fluid at the normal operating temperature is such that the fluid is retained on the rollers and disks of the T-CVT.

Traction fluids that are non-toxic to humans and posses a non-offensive odor, while also being inexpensive to manufacture are desirable.

While the large and heavy nature of T-CVT systems can be problematic, they do offer advantages that make them desirable, especially in terms of providing greater fuel economy in vehicles and machines. Generally, T-CVT systems provide at least 10% fuel efficiency over traditional automatic transmissions because the engine runs at its most efficient point independent of the vehicle speed. Since the traction fluid is responsible for the transfer of power to the wheels, the efficiency of a T-CVT system is related to $\mu_T$ and viscosity of the utilized traction fluid. Further, an increase in efficiency also allows for the reduction in size and weight of the T-CVT system.

Known traction fluids do not have acceptable physical properties. Particularly, some known traction fluids have a high $\mu_T$ at normal operating temperatures, but unacceptably high viscosities at low temperatures. Other known traction fluids have good low temperature viscosities, but the $\mu_T$ is unsatisfactory. Still other traction fluids have $\mu_T$ which are unacceptably dependent on temperature. Most known traction fluids suffer from difficult, expensive, and inefficient synthetic methods.

Exemplary known traction fluids include those based on 2,4-dicyclohexyl-2-methylpentane (DCMP) [CAS# 38970-72-8], which has a structure of:

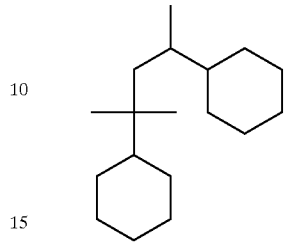

Another known traction fluid is made from santene and isosantene (called FLUID X). The structure of the main component of this traction fluid is as follows:

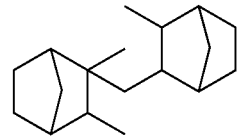

Accordingly, the inventors have recognized a new class of traction fluids which overcome one or more of these problems which allow more efficient T-CVT systems.

SUMMARY OF THE INVENTION

The present invention includes a traction fluid that includes a di-acid ester bridged dimer. Methods of using di-acid ester bridged dimers in traction fluids are also disclosed.

DETAILED DESCRIPTION

Figure 1A:
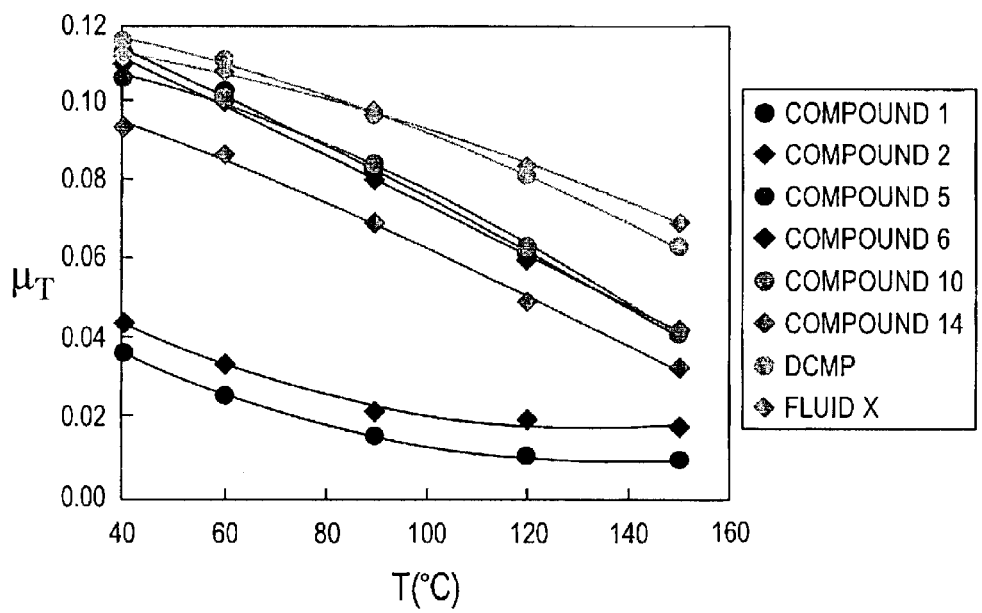
FIG. 1 compares the temperature dependence of the $\mu_T$ of the inventive traction fluids to that of the commercial fluids at a contact pressure of 1.27 GPa and slide-to-roll ratios of (a) 4% and (b) 1%.

The present invention is a traction fluid composition including a di-acid ester bridged dimer. The dimers are two cycloalkane or bicycloalkane moieties connected via a di-acid ester bridge.

Bridged dimers useful in the present invention are described by the general formula X—Y—Z, where X and Z are the same or different cycloalkane or bicycloalkane moieties and Y is a straight or branched di-acid ester bridge. The cycloalkane moieties may include cyclopentyl and cyclohexyl, while the bicycloalkane moieties may be bicyclo[2.2.1]heptanyl, bicyclo[3.1.1]heptanyl, bicyclo[4.1.0]heptanyl, bicyclo[2.2.2]octanyl, bicyclo[3.3.0]octanyl or bicyclo[3.2.1]octanyl.

The following generic structure describes some useful classes of compounds in the present invention:

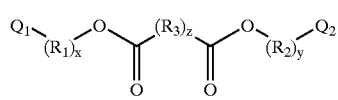

Formula I wherein $R_1$, $R_2$ and $R_3$ represent straight or branched alkyl groups with 1 to 8 carbons, x, y and z are independently 0 to 4. $R_1$, $R_2$ and $R_3$ may be substituted or unsubstituted wherein the substituents may be straight or branched alkyl, heteroatom or halogenated alkyl groups, where the number of substituents equals 0 to 2(x, y, z), respectively. The substituents may be independently selected.

$Q_1$ and $Q_2$ may be independently selected from the following formulae, where attachment may be at any accessible ring carbon:

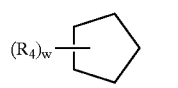

Formula II

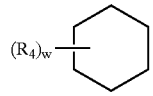

Formula III

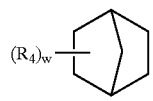

Formula IV

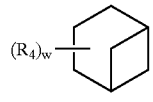

Formula V

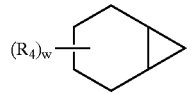

Formula VI

Formula VII

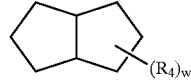

Formula VIII

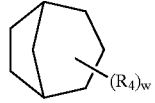

Formula IX wherein $R_4$ represents H, straight or branched alkyl substituents with 0 to 8 carbons, halogen, halogenated alkyl or alkyl groups including one or more heteroatoms, where w is the number of substituents. The substituents may be attached to any accessible ring carbon.

$Q_1$ and $Q_2$ may include the following moieties where attachment may be at any accessible carbon:

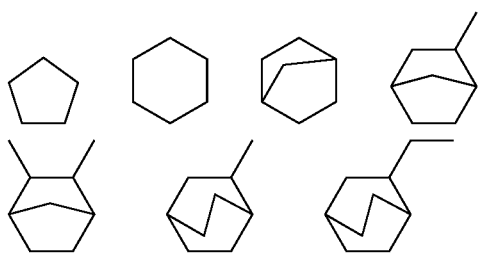

Useful compounds of the present invention are as follows:

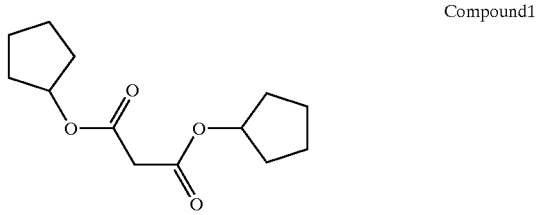

Compound 1

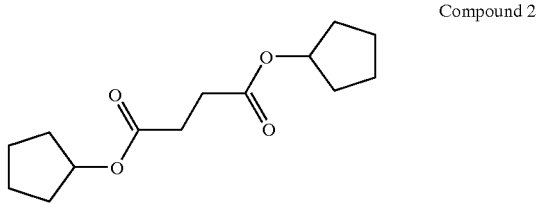

Compound 2

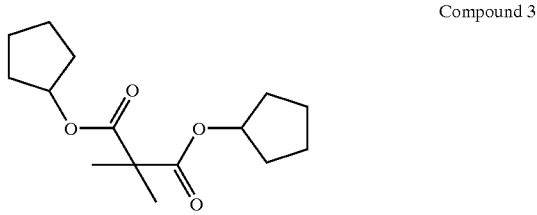

Compound 3

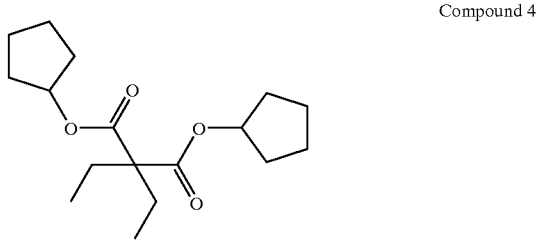

Compound 4

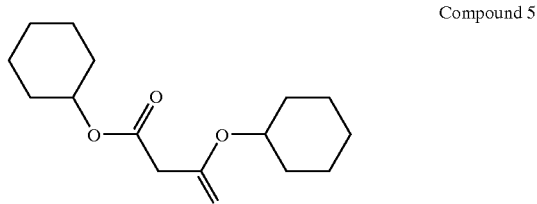

Compound 5

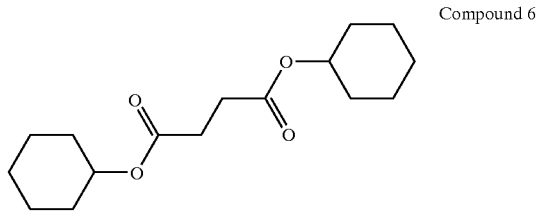

Compound 6

Compound 7
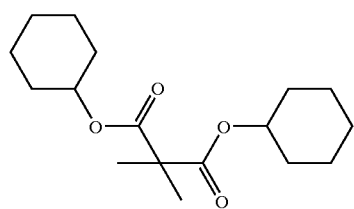
Compound 8
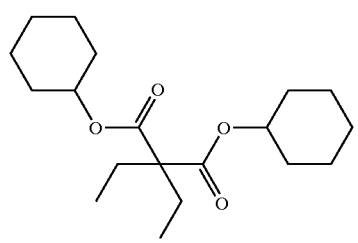
Compound 9
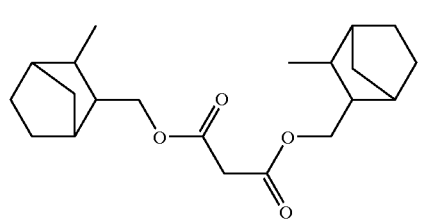
Compound 10
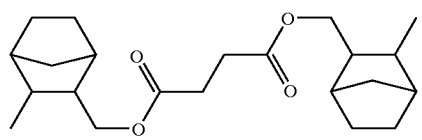
Compound 11
Compound 12
Compound 13
Compound 14
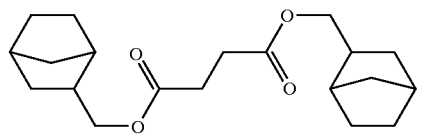
Compound 15
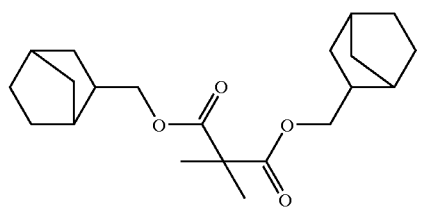
Compound 16
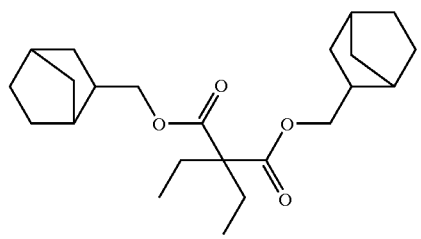
Compound 17
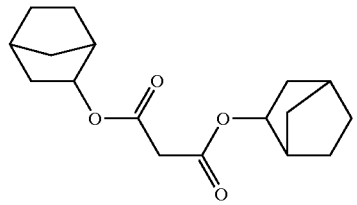
Compound 18
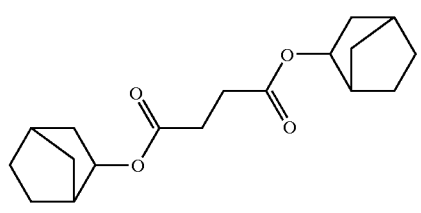
Compound 19
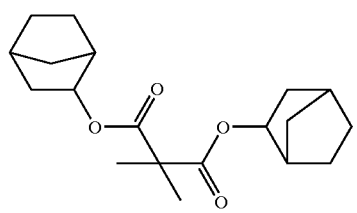
Compound 20
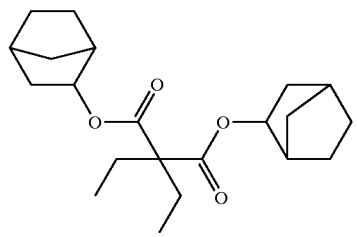

Compound 21

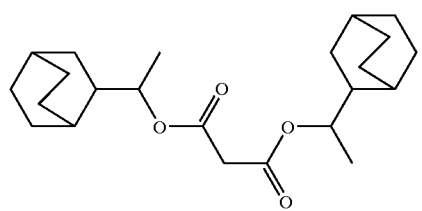

Compound 22

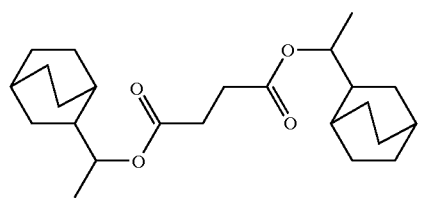

Compound 23

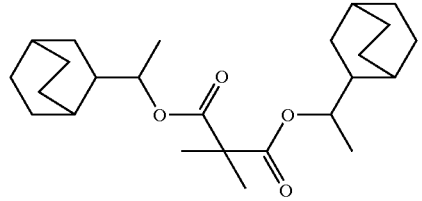

Compound 24

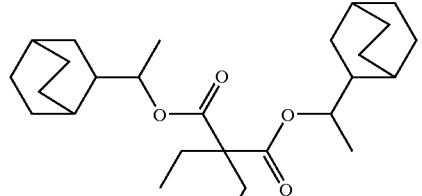

Compound 25

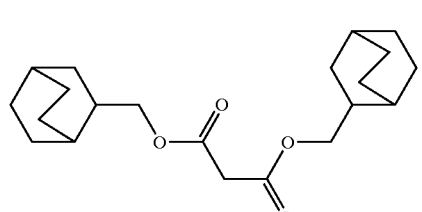

Compound 26

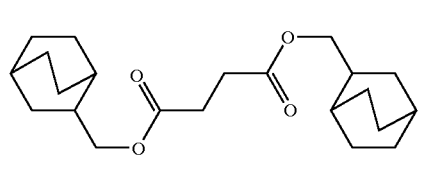

Compound 27

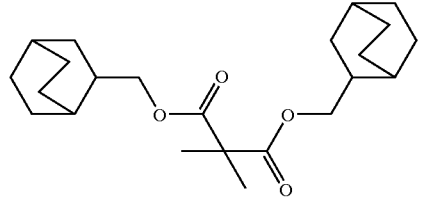

Compound 28

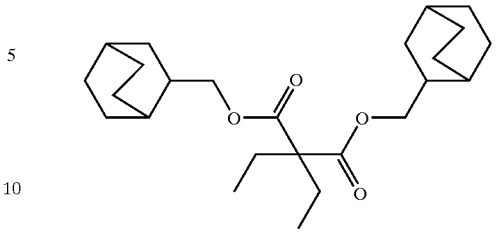

Names of Compounds 1–28 are found in Table 1.

TABLE 1

| | |
|---|---|
| Compound 1 | malonic acid, dicyclopentyl ester |
| Compound 2 | succinic acid, dicyclopentyl ester |
| Compound 3 | dimethylmalonic acid, dicyclopentyl ester |
| Compound 4 | diethylmalonic acid, cyclopentyl ester |
| Compound 5 | malonic acid, dicyclohexyl ester |
| Compound 6 | succinic acid, dicyclohexyl ester |
| Compound 7 | dimethylmalonic acid, dicyclohexyl ester |
| Compound 8 | diethylmalonic acid, cyclohexyl ester |
| Compound 9 | di-[3-methyl-bicyclo[2.2.1]hept-2-yl] methyl malonate |
| Compound 10 | di-[3-methyl-bicyclo[2.2.1]hept-2-yl] methyl succinate |
| Compound 11 | di-[3-methyl-bicyclo[2.2.1]hept-2-yl] methyl dimethylmalonate |
| Compound 12 | di-[3-methyl-bicyclo[2.2.1]hept-2-yl] methyl diethylmalonate |
| Compound 13 | di-[bicyclo[2.2.1]hept-2-yl] methyl malonate |
| Compound 14 | di-[bicyclo[2.2.1]hept-2-yl] methyl succinate |
| Compound 15 | di-[bicyclo[2.2.1]hept-2-yl] methyl dimethylmalonate |
| Compound 16 | di-[bicyclo[2.2.1]hept-2-yl] methyl diethylmalonate |
| Compound 17 | di-[bicyclo[2.2.1]hept-2-yl] malonate |
| Compound 18 | di-[bicyclo[2.2.1]hept-2-yl] succinate |
| Compound 19 | di-[bicyclo[2.2.1]hept-2-yl] dimethylmalonate |
| Compound 20 | di-[bicyclo[2.2.1]hept-2-yl] diethylmalonate |
| Compound 21 | di-1-[bicyclo[2.2.2]oct-2-yl] ethyl malonate |
| Compound 22 | di-1-[bicyclo[2.2.2]oct-2-yl] ethyl succinate |
| Compound 23 | di-1-[bicyclo[2.2.2]oct-2-yl] ethyl dimethylmalonate |
| Compound 24 | di-1-[bicyclo[2.2.2]oct-2-yl] ethyl diethylmalonate |
| Compound 25 | di-[bicyclo[2.2.2]oct-2-yl] methyl malonate |
| Compound 26 | di-[bicyclo[2.2.2]oct-2-yl] methyl succinate |
| Compound 27 | di-[bicyclo[2.2.2]oct-2-yl] methyl dimethylmalonate |
| Compound 28 | di-[bicyclo[2.2.2]oct-2-yl] methyl diethylmalonate |

The compounds of the present invention may be synthesized by a variety of different methods. A common method involves the acid catalyzed reaction of a carboxylic acid and an alcohol shown in Reaction A.

$$R(C(O)OH)_2 + 2[HOR'] \xrightleftharpoons{H^+} R(C(O)OR')_2 + 2[H_2O]$$

R is a connector for the two acid moieties and R' represents the substituent that is to be connected by the di-acid ester bridge. This reaction is catalyzed by strong acids, such as sulfuric acid or p-toluenesulfonic acid (TsOH) and is reversible. The selection of the acid will be dictated by solubility in the desired solvent system. Thus, water should be removed to force the reaction to completion. For example, water may be removed through the use of a Dean-Stark trap. Steric effects of substituents may also slow the reaction. The reaction delivers acceptable yields in a relatively short period of time.

Di-acid esters may also be synthesized through the reaction of an acyl halide and an alcohol shown in Reaction B.

Reaction B $$R(C(O)Cl)_2 + 2[HOR'] \rightarrow R(C(O)OR')_2 + 2[HCl]$$

This reaction is reversible; consequently, an acid scavenger may be used to force the reaction to completion. Pyridine is an exemplary scavenger for HCl. Reaction B is generally preferred when dealing with bulky substituents because the reaction gives high yields. But many acid halides are difficult to obtain commercially and synthesis may be time consuming. Overall, this synthetic approach is slower than the acid catalyzed synthetic approach.

Although not preferred a trans-esterification synthetic approach may also be used; likewise, any other synthetic approach that yields di-acid esters may also be suitable.

The starting materials for Reaction 1 include dicarboxylic acids connected by a straight or branched chain of 0 to 5 carbons, where the branches may be up to 10 carbons in length. A variety of heteroatom and halogens may also be substituents on the connecting chain. Exemplary dicarboxylic acids include those shown below:

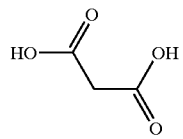
Malonic Acid (MA)

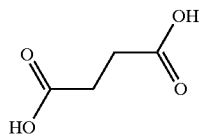
Succinic acid (SA)

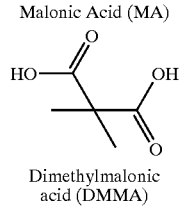
Dimethylmalonic acid (DMMA)

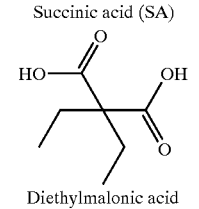
Diethylmalonic acid (DEMA)

The starting materials for Reaction 1 include alcohols of the cyclic and bicyclic moieties shown above in Formulae II–IX. Exemplary alcohols include those shown below:

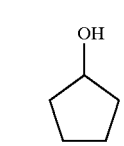
Cyclopentanol (A1)

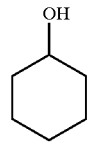
Cyclohexanol (A2)

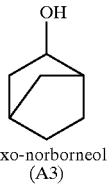
(exo-norborneol (A3)

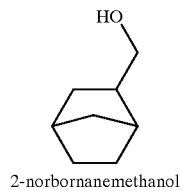
2-norbornanemethanol

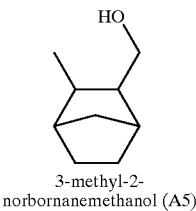
3-methyl-2-norbornanemethanol (A5)

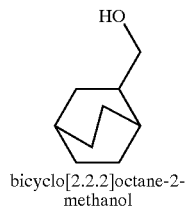
bicyclo[2.2.2]octane-2-methanol

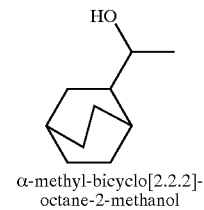
α-methyl-bicyclo[2.2.2]-octane-2-methanol

Alcohols that are not readily available may be synthesized through a hydrogenation reaction combining an alkenyl aldehyde or alkenyl ketone with a cycloalkene or a bicycloalkene. Hydrogenation is usually carried out in the presence of a catalyst in a pressurized $H_2$ atmosphere. Suitable catalysts include nickel, rhodium, ruthenium, palladium, platinum, and the like. Preferred catalysts include 0.1% to 20% wt % of nickel on diatomite, silica alumina or other substrate. Suitable $H_2$ pressures include 50 to 3000 psi for 0.5 to 10 hours. The temperature range for the hydrogenation reaction is −100° C. to 400° C.

Other starting materials and other synthetic methods may be utilized as warranted by considerations of reaction efficiency, cost of starting materials, and ease of handling of starting materials and reaction products.

Working Examples

All of the chemicals were used as received from Sigma-Aldrich and Mallinckrodt. The alcohols used in this study were cyclopentanol (A1), reagent grade, cyclohexanol (A2), 98%, exo-norborneol (A3), 98%, 2-norbornanemethanol (A4), 97%, and 3-methyl-2-norbornane-methanol (A5), 93%,. The di-acids used were malonic acid (MA), 99%, reagent grade succinic acid (SA), dimethylmalonic acid (DMMA), 98%, and diethylmalonic acid (DEMA), 98%. Reagent grade p-toluenesulfonic acid monohydrate (TsOH), 98.5%, was used as a catalyst. The desiccant, anhydrous magnesium sulfate, 99%, was also used as received.

The di-acid esters were synthesized in 250 or 500 mL round bottom flasks connected to Dean-Stark traps and condensers. Reaction ratios were arranged so that there was approximately a 10% excess of alcohol beyond what would be required by stochiometry. The best results were obtained when the reaction set-ups were purged with dry nitrogen gas and a nitrogen gas atmosphere was maintained throughout the reaction period. Table 2 provides the quantities of materials used in each reaction.

TABLE 2

Starting materials for synthesizing traction fluids

| Product | Compound 1 | Compound 2 | Compound 3 | Compound 4 |
|---|---|---|---|---|
| Alcohol | A1 | A1 | A1 | A1 |
| g | 69 | 65.7 | 62.6 | 57.3 |
| (moL) | (0.80) | (0.76) | (0.73) | (0.67) |
| Di-acid | MA | SA | DMMA | DEMA |
| g | 37.9 | 41 | 43.4 | 48.5 |
| (moL) | (0.36) | (0.35) | (0.33) | (0.30) |
| TsOH, g | 1.2 | 1.2 | 1.2 | 1.2 |
| Xylene, g | 140 | 140 | 140 | 140 |

| Product | Compound 5 | Compound 6 | Compound 7 | Compound 8 |
|---|---|---|---|---|
| Alcohol | A2 | A2 | A2 | A2 |
| g | 72.8 | 69.6 | 66.7 | 61.5 |
| (moL) | (0.73) | (0.70) | (0.67) | (0.61) |
| Di-acid | MA | SA | DMMA | DEMA |
| g | 34.4 | 37.3 | 40 | 44.7 |
| (moL) | (0.33) | (0.32) | (0.30) | (0.28) |
| TsOH, g | 1.2 | 1.2 | 1.2 | 1.2 |
| Xylene, g | 140 | 140 | 140 | 140 |

| Product | Compound 9 | Compound 10 | Compound 11 | Compound 12 |
|---|---|---|---|---|
| Alcohol | A3 | A3 | A3 | A3 |
| g | 70.1 | 68 | 65.5 | 60.5 |
| (moL) | (0.63) | (0.61) | (0.58) | (0.54) |
| Di-acid | MA | SA | DMMA | DEMA |
| g | 29 | 32.3 | 34.5 | 39 |
| (moL) | (0.28) | (0.27) | (0.26) | (0.24) |
| TsOH, g | 1.2 | 1.2 | 1.2 | 1.2 |
| Xylene, g | 140 | 141 | 140 | 140 |

| Product | Compound 13 | Compound 14 | Compound 15 | Compound 16 |
|---|---|---|---|---|

TABLE 2-continued

Starting materials for synthesizing traction fluids

| Alcohol | A4 | A4 | A4 | A4 |
|---|---|---|---|---|
| g | 73 | 70.6 | 67.7 | 63.6 |
| (moL) | (0.60) | (0.56) | (0.54) | (0.50) |
| Di-acid | MA | SA | DMMA | DEMA |
| g | 27 | 29.4 | 32.2 | 36.6 |
| (moL) | (0.26) | (0.25) | (0.24) | (0.23) |
| TsOH, g | 1.2 | 1.2 | 1.2 | 1.2 |
| Xylene, g | 140 | 141 | 140 | 140 |

| Product | Compound 17 | Compound 18 | Compound 19 | Compound 20 |
|---|---|---|---|---|
| Alcohol | A5 | A5 | A5 | A5 |
| g | 75 | 72.4 | 70 | 65.9 |
| (moL) | (0.54) | (0.52) | (0.50) | (0.47) |
| Di-acid | MA | SA | DMMA | DEMA |
| g | 25 | 27.8 | 30 | 34.2 |
| (moL) | (0.24) | (0.24) | (0.23) | (0.21) |
| TsOH, g | 1.2 | 1.2 | 1.2 | 1.2 |
| Xylene, g | 140 | 140 | 140 | 140 |

The calculated quantities of starting materials were weighed directly into the round bottom flasks. Dry nitrogen was used to purge the condenser and Dean-Stark trap before attachment of the flask to the assembly. The flask and contents were heated with an external heating mantle while stirring was achieved with a magnetic stirring bar. Through out the reactions, the contents were continuously kept under a nitrogen atmosphere. When the volumetric amount of water collected in the trap approximately equaled the calculated stochiometric water yield, the reflux was halted.

After cooling, the solutions were poured into a separatory funnel, washed twice with saturated sodium bicarbonate solutions then washed twice with saturated sodium chloride solutions. The xylene solutions were then poured into bottles, anhydrous magnesium sulfate (a desiccant) was added, and the mixtures were allowed to dry for 12 hours. After drying, the mixtures were separated from the desiccant through vacuum filtration. The mixture was transferred to a 500 mL round bottom flask, where the xylene was removed under vacuum (≈0.5 torr) using a rotary evaporator. The mixture was then vacuum distilled at 0.5 torr. Fractions were collected in the temperature windows according to the following Table 3:

TABLE 3

| Compound 1 | Compound 2 | Compound 3 | Compound 4 |
|---|---|---|---|
| 110 ± 10 | 131 ± 10 | 125 ± 10 | 146 ± 10 |
| Compound 5 | Compound 6 | Compound 7 | Compound 8 |
| 134 ± 10 | 155 ± 10 | 149 ± 10 | 169 ± 10 |
| Compound 9 | Compound 10 | Compound 11 | Compound 12 |
| 186 ± 12 | 204 ± 12 | 199 ± 12 | 218 ± 12 |
| Compound 13 | Compound 14 | Compound 15 | Compound 16 |
| 175 ± 12 | 194 ± 12 | 188 ± 12 | 207 ± 12 |
| Compound 17 | Compound 18 | Compound 19 | Compound 20 |
| 150 ± 10 | 176 ± 12 | 169 ± 10 | 189 ± 12 |

The products were analyzed using GC-MS. Product yield was measured gravimetrically as a wt % function of anticipated stochiometric yield shown in Table 4.

TABLE 4

Reaction Yields

| Di-acid Ester | Product Yield wt. % | Yield Purity % | FP/MP ° C. | Physical Appearance |
|---|---|---|---|---|
| Compound 1 | 71 | >99 | <−60 | pale yellow |
| Compound 2 | 72 | >99 | −22 ± 4 | pale yellow |
| Compound 3 | 60 | 96 | <−60 | amber |
| Compound 4 | 1 | ISQ | ISQ | clear |
| Compound 5 | 75 | >99 | −37 ± 4 | clear |
| Compound 6 | 78 | >99 | −31 ± 3 | clear |
| Compound 7 | 62 | 94 | −44 ± 5 | clear |
| Compound 8 | <1 | ISQ | ISQ | clear |
| Compound 9 | 52 | 91 | −31 ± 4 | brown |
| Compound 10 | 79 | >99 | −16 ± 4 | brown |
| Compound 11 | 74 | >99 | −26 ± 3 | brown |
| Compound 12 | <1 | ISQ | ISQ | brown |
| Compound 13 | 62 | >99 | −40 ± 4 | light brown |
| Compound 14 | 73 | >99 | −23 ± 3 | light brown |
| Compound 15 | 74 | >99 | NA | solid @ room temp |
| Compound 16 | <1 | 7 | ISQ | NA |
| Compound 17 | 62 | 98 | −33 ± 4 | light brown |
| Compound 18 | 61 | 97 | NA | solid @ room temp |
| Compound 19 | 57 | 97 | −12 ± 3 | brown |
| Compound 20 | <1 | 3 | ISQ | NA |

Due to the yield purity and resulting insufficient sample quantity (ISQ) of distilled Compound 4, Compound 8, Compound 12, Compound 16, and Compound 20, additional physical testing was not performed. Due to the di-acid esters solid state at room temperature, additional physical testing was also not performed on distilled samples Compound 15 and Compound 8.

Traction Coefficients

The traction coefficient, $\mu_T$, of each of Compounds 1, 2, 5, 6, 10 and 14 ("the tested COMPOUNDS") and the commercial traction fluids, FLUID X and DCMP, were obtained with a PCS Instruments Model M110 ball-on-disc mini-traction apparatus. Traction tests on the fluids were made using ¾-in 52100 steel balls at a maximum Hertzian contact pressure (P) of 0.992, 1.15, and 1.27 GPa with a fluid entrainment velocity of ~2.8 m/s. At each contact pressure, $\mu_T$ was measured at temperatures ranging between 40° C. and 150° C.

Figure 1B:
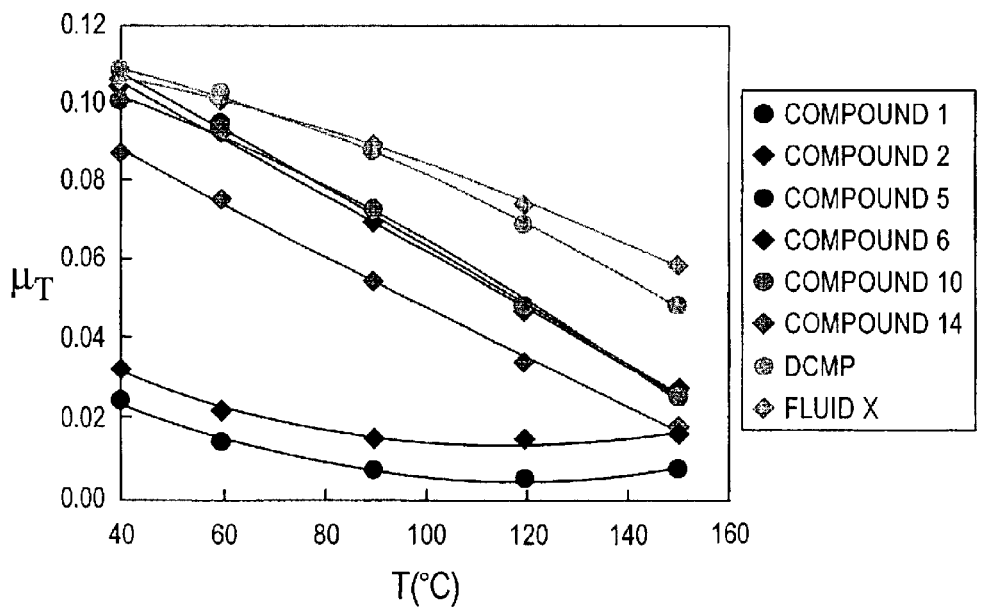
Figure 2A:
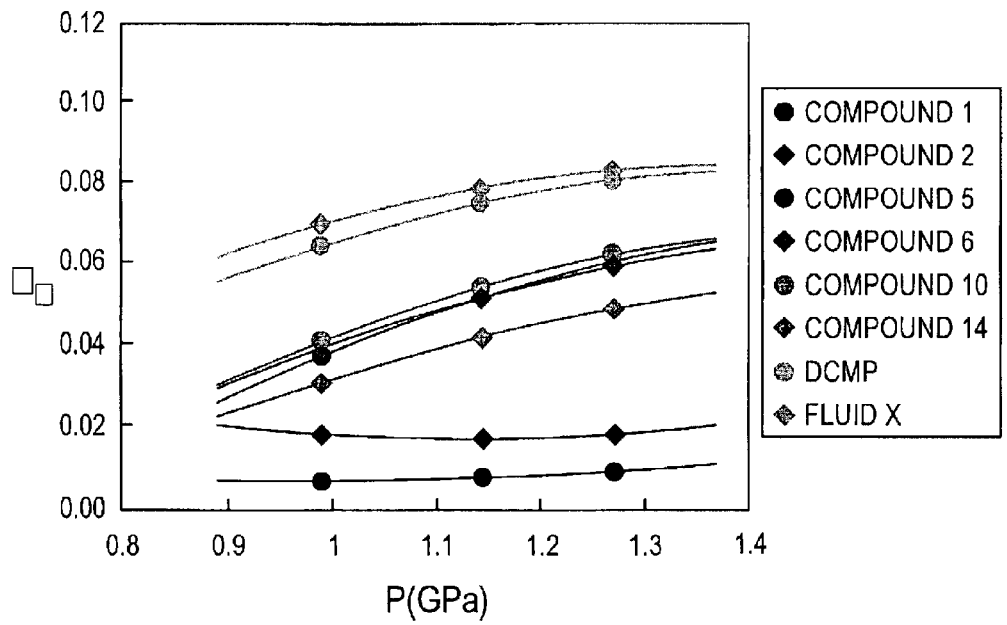
FIG. 2 compares the pressure dependence of the $\mu_T$ of the inventive traction fluids to that of the commercial fluids at a temperature of 120° C. and slide-to-roll ratios of (a) 4% and (b) 1%.
Figure 2B:
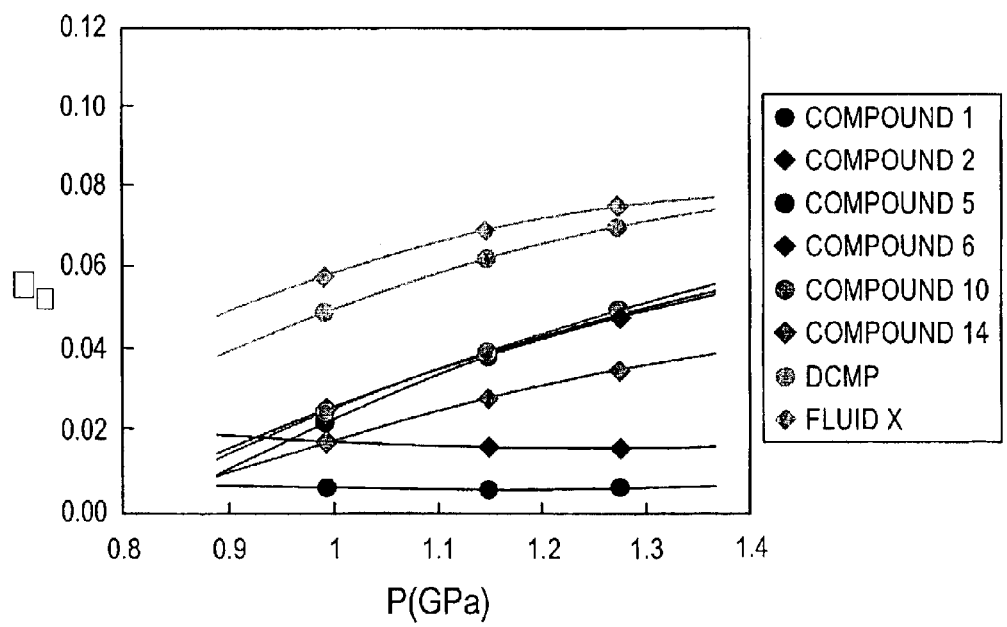

The temperature dependence of the traction coefficients was measured with a contact pressure of 1.27 GPa and slide-to-roll ratios (SRR) of 4% and 1%, with the results shown in FIGS. 1(a) and 1(b). The pressure dependence of the traction coefficients were measured at a temperature of 120° C. and SRR of 4% and 1%, with the results shown in FIGS. 2(a) and 2(b). These Figures reveal that the commercial traction fluids have a higher $\mu_T$ than the tested COMPOUNDS over the range of temperatures and pressures.

Viscosities and Pour Points

The viscosity of each of the tested COMPOUNDS and FLUID X were obtained with a TA Instrument's AR1000 controlled shear rheometer. All the measurements were made using a 4 cm diameter parallel plate geometry with a 100 μm gap maintaining a constant shear rate of 10 s⁻¹, while ramping the temperature at 0.5° C./min between −15° and 120° C.

Figure 3:
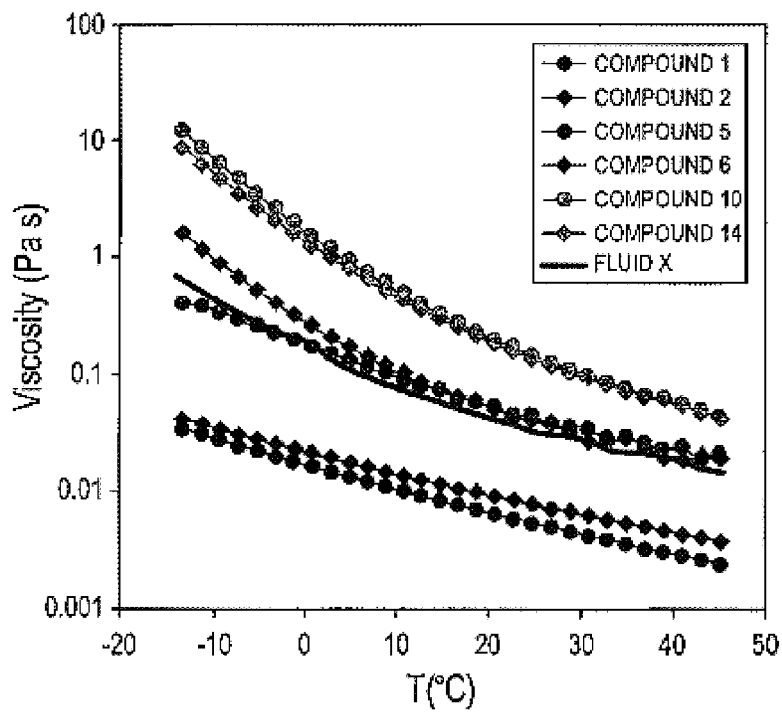
FIG. 3 compares the temperature viscosities of the COMPOUNDS 1, 2, 5, 6, 10 and 14 to that of the commercial traction fluid FLUID X.

The temperature dependence of the viscosities was measured, with the results shown in FIG. 3. This Figure reveals that COMPOUNDS 1, 2 and 5 have viscosities at −15° C. that are lower than FLUID X.

Figure 4:
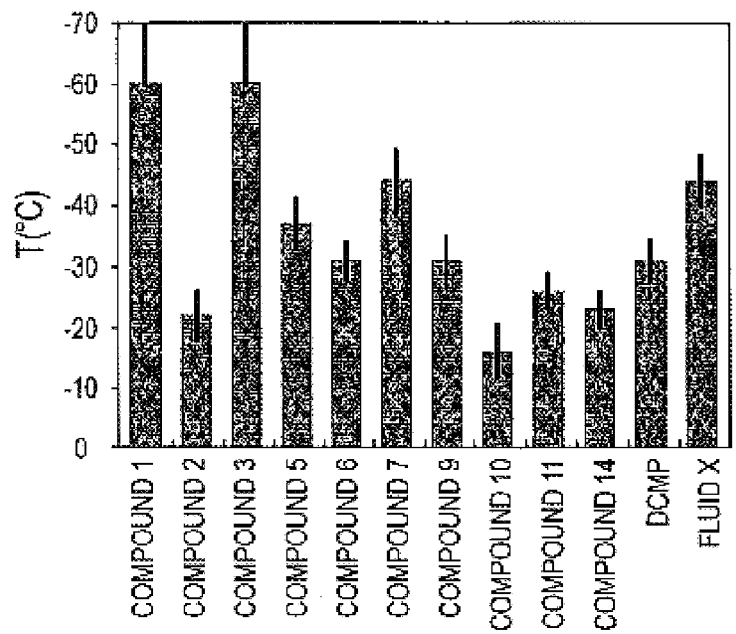
FIG. 4 compares the freezing point of the COMPOUNDS 1–3, 5–7, 9–11 and 14 to that of the commercial traction fluid FLUID X and DCMP.

The freezing point of each of the tested COMPOUNDS and FLUID X was determined, as shown in FIG. 4. The Figure reveals that COMPOUNDS 1, 3, 5, 7 and 9 have freezing points below about −30° C., with COMPOUNDS 1 and 3 with freezing point of less than about −60° C.

Taken together, the traction coefficient, viscosity and pour point data suggest that the di-acid ester bridged dimers would be suitable as pour point depressants for a traction fluid.

Fragrance

Unexpectedly, the di-acid ester bridged compounds have a fragrance which is not offensive to the human sense of smell. In fact, several of the compounds have a scent reminiscent of pink bubble gum. Consequently, these compounds may be utilized to sanitize odors normally deemed to be offensive by including one or more of these compounds in a composition in need santizing.

While the invention has been specifically described in connection with certain specific embodiments thereof, it is to be understood that this is by way of illustration and not of limitation, and the scope of the appended claims should be construed as broadly as the prior art will permit.

What is claimed is:

1. A composition comprising a traction fluid that includes at least one compound according to the following formula:

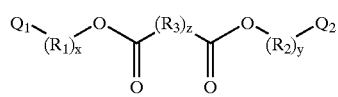

wherein $R_1$, $R_2$ and $R_3$ represent straight or branched, substituted or unsubstituted alkyl groups with 1 to 8 carbons, where substituents include straight or branched alkyl, heteoatom or halogenated alkyl groups, x, y and z are independently 0 to 4 and $Q_1$ and $Q_2$ are independently selected from the following groups:

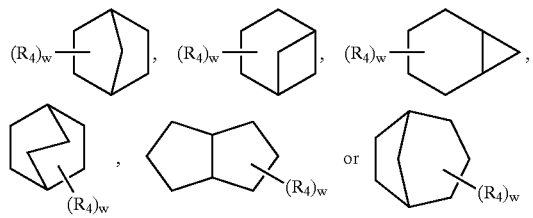

and are attached at any accessible carbon, wherein $R_4$ represents H, straight or branched alkyl substituents with 0 to 8 carbons, halogen, halogenated alkyl or alkyl groups including one or more heteroatoms, where w is the number of substituents and wherein the substituents may be attached to any accessible ring carbon.

2. The composition of claim 1, wherein Q1 and Q2 are independently selected from the following groups:

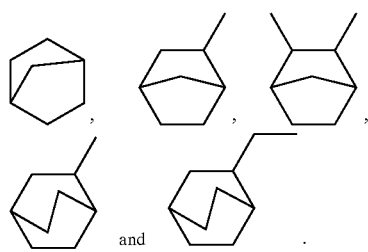

3. The composition of claim 2, wherein the traction fluid includes at least one compound selected from:

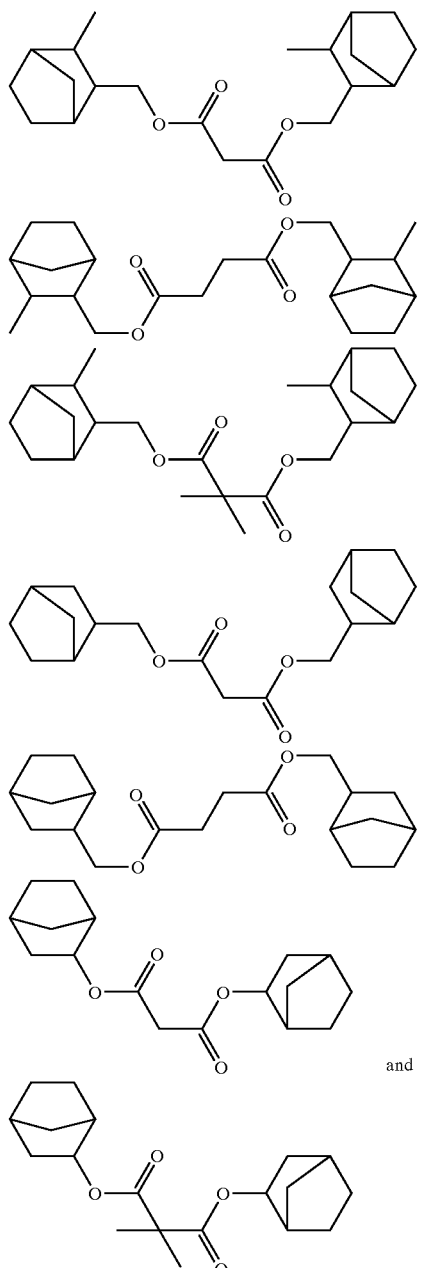

and

4. The composition of claim 3, wherein the traction fluid includes:

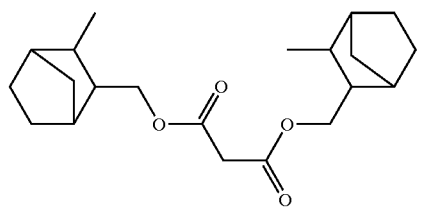

5. The composition of claim 1, wherein the traction includes at least one compound selected from:

di-[3-methyl-bicyclo[2.2.1]hept-2-yl]methyl malonate,
di-[3-methyl-bicyclo[2.2.1]hept-2-yl]methyl succinate, di-[3-methyl-bicyclo[2.2.1]hept-2-yl]methyl dimethylmalonate,
di-[3-methyl-bicyclo[2.2.1]hept-2-yl]methyl diethylmalonate,
di-[bicyclo[2.2.1]hept-2-yl]methyl malonate,
di-[bicyclo[2.2.1]hept-2-yl]methyl succinate,
di-[bicyclo[2.2.1]hept-2-yl]methyl dimethylmalonate,
di-[bicyclo[2.2.1]hept-2-yl]methyl diethylmalonate,
di-[bicyclo[2.2.1]hept-2-yl]malonate,
di-[bicyclo[2.2.1]hept-2-yl]succinate,
di-[bicyclo[2.2.1]hept-2-yl]dimethylmalonate,
di-[bicyclo[2.2.1]hept-2-yl]diethylmalonate,
di-1-[bicyclo[2.2.2]oct-2-yl]ethyl malonate,
di-1-[bicyclo[2.2.2]oct-2-yl]ethyl succinate,
di-1-[bicyclo[2.2.2]oct-2-yl]ethyl dimethylmalonate,
di-1-[bicyclo[2.2.2]oct-2-yl]ethyl diethylmalonate,
di-[bicyclo[2.2.2]oct-2-yl]methyl malonate,
di-[bicyclo[2.2.2]oct-2-yl]methyl succinate,
di-[bicyclo[2.2.2]oct-2-yl]methyl dimethylmalonate and
di-[bicyclo[2.2.2]oct-2-yl]methyl diethylmalonate.

6. A method of operating a transmission, comprising: lubricating a toroidal continuously variable transmission with a traction fluid that includes at least one compound according to the following formula:

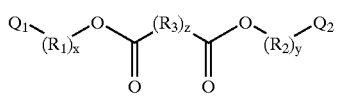

wherein $R_1$, $R_2$ and $R_3$ represent straight or branched, substituted or unsubstituted alkyl groups with 1 to 8 carbons, where substituents include straight or branched alkyl, heteroatom or halogenated alkyl groups, x, y and z are independently 0 to 4 and $Q_1$ and $Q_2$ are independently selected from the following groups:

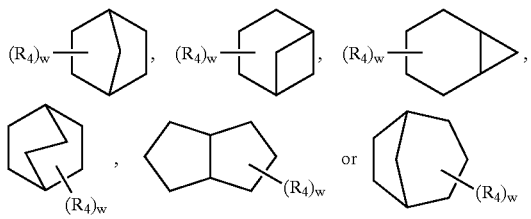

and are attached at any accessible carbon, wherein $R_4$ represents H, straight or branched alkyl substituents with 0 to 8 carbons, halogen, halogenated alkyl or alkyl groups including one or more heteroatoms, where w is the number of substituents and wherein the substituents may be attached to any accessible ring carbon.

7. The method of claim 6, wherein Q1 and Q2 are independently selected from the following groups:

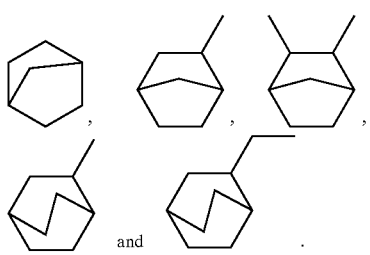

8. The method of claim 7, wherein the traction fluid includes at least one compound selected from:

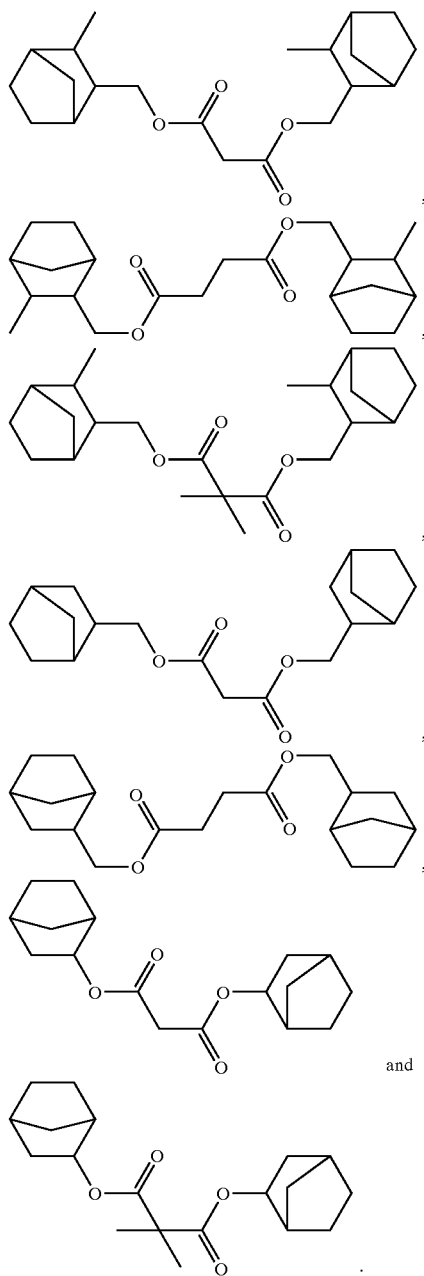

and

9. The method of claim 8, wherein the traction fluid includes:

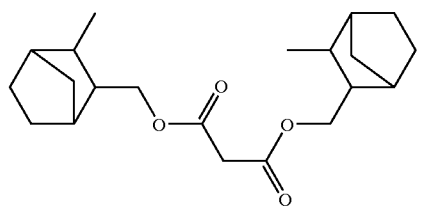

10. A method of obscuring an offensive odor in a composition, comprising: sanitizing the composition with an effective amount of a compound according to the following formula:

17

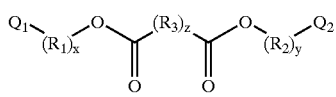

wherein $R_1$, $R_2$ and $R_3$ represent straight or branched, substituted or unsubstituted alkyl groups with 1 to 8 carbons, where substituents include straight or branched alkyl, heteoatom or halogenated alkyl groups, x, y and z are independently 0 to 4 and $Q_1$ and $Q_2$ are independently selected from the following groups:

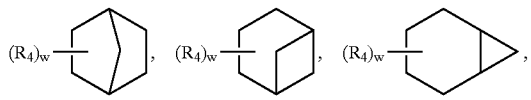

18

-continued

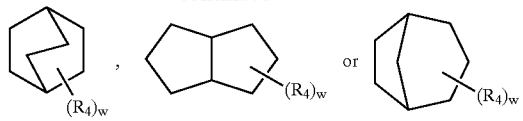

and are attached at any accessible carbon, wherein $R_4$ represents H, straight or branched alkyl substituents with 0 to 8 carbons, halogen, halogenated alkyl or alkyl groups including one or more heteroatoms, where w is the number of substituents and wherein the substituents may be attached to any accessible ring carbon.

* * * * *